United States Patent
Limketkai et al.

(12) 
(10) Patent No.: US 10,736,967 B2
(45) Date of Patent: Aug. 11, 2020

(54) METHOD OF PREPARING CYCLODEXTRIN COMPLEXES

(71) Applicant: Panaceanano, Inc., Laguna Niguel, CA (US)

(72) Inventors: Benjie N. Limketkai, Hesperia, CA (US); Youssry Y. Botros, Laguna Niguel, CA (US)

(73) Assignee: PanaceaNano, Inc., Laguna Niguel, CA (US)

( * ) Notice: Subject to any disclaimer, the term of this patent is extended or adjusted under 35 U.S.C. 154(b) by 0 days.

(21) Appl. No.: 15/395,138

(22) Filed: Dec. 30, 2016

(65) Prior Publication Data

US 2017/0189551 A1 Jul. 6, 2017

Related U.S. Application Data

(60) Provisional application No. 62/274,962, filed on Jan. 5, 2016.

(51) Int. Cl.
| | | |
|---|---|---|
| C08B 37/00 | (2006.01) |
| A61K 47/48 | (2006.01) |
| C08B 37/16 | (2006.01) |
| A61K 47/69 | (2017.01) |
| A61K 31/60 | (2006.01) |
| A61K 31/192 | (2006.01) |

(52) U.S. Cl.
CPC ...... *A61K 47/48969* (2013.01); *A61K 31/192* (2013.01); *A61K 31/60* (2013.01); *A61K 47/6951* (2017.08); *C08B 37/0015* (2013.01)

(58) Field of Classification Search
CPC ..................... A61K 47/48969; A61K 31/192
USPC ......................................................... 536/124
See application file for complete search history.

(56) References Cited

U.S. PATENT DOCUMENTS

| | | |
|---|---|---|
| 2,886,446 A | 5/1959 | Kramer et al. |
| 3,258,400 A | 6/1966 | Houlihan |
| 3,920,849 A | 11/1975 | Marmo et al. |
| 3,939,099 A | 2/1976 | Tusa et al. |
| 4,252,986 A | 2/1981 | Klein et al. |
| 4,303,787 A | 12/1981 | Horikoshi et al. |
| 4,384,898 A | 5/1983 | Okada et al. |
| 4,568,560 A | 2/1986 | Schobel |
| 4,808,232 A | 2/1989 | Beesley |
| 4,835,105 A | 5/1989 | Seres et al. |
| 4,849,400 A | 7/1989 | King |
| 5,051,305 A | 9/1991 | Whitaker, Sr. |
| 5,238,915 A | 8/1993 | Fuwa et al. |
| 6,110,449 A | 8/2000 | Bacon et al. |
| 6,172,037 B1 | 1/2001 | Perring et al. |
| 6,177,413 B1 | 1/2001 | Blahunt |
| 6,458,754 B1 | 10/2002 | Velazquez et al. |
| 6,558,706 B2 | 5/2003 | Kantor et al. |
| 6,660,804 B1 | 12/2003 | Weltrowski et al. |
| 8,709,072 B2 | 4/2014 | Rahi et al. |
| 8,871,473 B2 | 10/2014 | Wu |
| 9,085,460 B2 | 7/2015 | Stoddart et al. |
| 9,399,803 B2 | 7/2016 | Stoddart et al. |
| 2003/0092600 A1 | 5/2003 | Shepherd, Jr. |
| 2005/0255069 A1 | 11/2005 | Muller |
| 2008/0054089 A1 | 3/2008 | Oldfield et al. |
| 2008/0206823 A1 | 8/2008 | Jacobson et al. |
| 2011/0052650 A1 | 3/2011 | Morris et al. |
| 2012/0070904 A1 | 3/2012 | Stoddart et al. |
| 2013/0171228 A1 | 7/2013 | Morris |
| 2013/0313193 A1 | 11/2013 | Nair et al. |
| 2014/0105842 A1 | 4/2014 | Pan et al. |
| 2014/0220112 A1 | 8/2014 | Szoka, Jr. et al. |
| 2014/0311297 A1 | 10/2014 | Stoddart et al. |
| 2015/0150981 A1 | 6/2015 | Gref et al. |
| 2015/0322174 A1 | 11/2015 | Stoddart et al. |
| 2017/0136128 A1 | 5/2017 | Hartlieb et al. |
| 2017/0189890 A1 | 7/2017 | Holcroft et al. |
| 2017/0203073 A1 | 7/2017 | Dor-Zidon |
| 2018/0147284 A1 | 5/2018 | Orellana-Tavra et al. |

FOREIGN PATENT DOCUMENTS

| | | |
|---|---|---|
| CN | 104888235 A | 9/2015 |
| JP | H05-076756 A | 3/1993 |
| WO | 2007035596 A2 | 3/2007 |

(Continued)

OTHER PUBLICATIONS

Li et al.; CN105153328 A; Dec. 16, 2015 (Machine-English Translation).*
An et al. (J. Am. Chem. Soc. 2009, 131, 8376-8377).*
Lu, et al.; "Study on a new cyclodextrin based metal-organic framework with chiral helices"; Inorganic Chemistry Communications 61; Elsevier; 2015; pp. 48-52.
Michida, et al.; "Crystal growth of cyclodextrin-based metal-organic framework with inclusion of ferulic acid"; Crystal Research & Technology; Wiley Online Library; 2015; pp. 556-559.
Wind, et al.; "Engineering of factors determining a-amylase and cyclodextrin glycosyltransferase specificity in the cyclodextrin glycosyltransferase from Thermoanaerobacterium thermosulfurigenes EM1"; Jan. 6/Feb. 23, 1998; pp. 598-605.

(Continued)

*Primary Examiner* — Shaojia A Jiang
*Assistant Examiner* — Michael C Henry (57) ABSTRACT

Aspects of the disclosure feature a method that comprises preparing an agent-cyclodextrin complex. Preparing the agent-cyclodextrin complex includes contacting a first composition comprising an agent with a porous cyclodextrin-metal organic framework to form a second composition comprising an agent-cyclodextrin-metal organic framework complex, the cyclodextrin-metal organic framework including a plurality of cyclodextrin molecules and at least one metal cation. Preparing the agent-cyclodextrin complex also includes dissolving the agent-cyclodextrin-metal organic framework complex in an aqueous solvent to form a third composition including the agent-cyclodextrin complex.

20 Claims, 4 Drawing Sheets

(56) References Cited

FOREIGN PATENT DOCUMENTS

| WO | 2014095427 A1 | 6/2014 |
|---|---|---|
| WO | 2016010522 A1 | 1/2016 |

OTHER PUBLICATIONS

McKinlay, et al.; "BioMOFs: Metal-Organic Frameworks for Biological and Medical Applications"; 2010; pp. 6260-6266.
Smaldone, et al.; "Metal-Organic Frameworks from Edible Natural Products"; 2010; pp. 8630-8634.
Gassensmith, et al.; "Strong and Reversible Binding of Carbon Dioxide in a Green Metal—Organic Framework"; 2011; pp. 15312-15315.
Forgan, et al.; "Nanoporous Carbohydrate Metal—Organic Frameworks"; 2012; pp. 406-417.
Gassensmith, et al.; "A Metal—Organic Framework-Based Material for Electrochemical Sensing of Carbon Dioxide"; 2014; pp. 8277-8282.
Gassensmith, et al.; "A Metal—Organic Framework-Based Material for Electrochemical Sensing of Carbon Dioxide"; Supplementary Information; 2014; pp. S1-S12.
Liu, et al.; "Second-Sphere Coordination Revisited"; 2014; pp. 315-320.
Liu, et al.; "Extended metal-carbohydrated frameworks"; 2014; pp. 1-14.
Loftsson, et al.; "Cyclodextrins in topical drug formulations: theory and practice"; Elsevier; International Journal of Pharmaceutics 225; www.elsevier.com/locate/ijpharm; Apr. 20, 2001; 16 pgs.
Matsuda, et al.; "Cyclodextrins in transdermal and rectal delivery"; Elsevier; Advanced Drug Delivery Reviews 36; 1999; 19 pgs.
Bernini, et al.; "Screening of bio-compatible metal-organic framesworks as potential drug carriers using Monte Carlo simulations"; Journal of Materials Chemistry B; Royal Society of Chemistry; www.rsc.org/MaterialsB; DOI: 10.1039/c3tb21328e; Nov. 22, 2013; 9 pgs.
Sha, et al.; "Synthesis and structure of new carbohydrate metal-organic frameworks and inclusion complexes"; Elsevier; Journal of Molecular Structure; www/elsevier.com; Aug. 13, 2015; 6 pgs.
Sha, et al.; "Unprecedented α-cyclodextrin metal-organic frameworks with chirality: Structure and drug adsorptions"; Elsevier; Polyhedron; www.elsevier.com/locate/poly; Oct. 19, 2016; 7 pgs.
Sha, et al.; "Nontoxic and renewable metal-organic framework based on α-cyclodextrin with efficient drug delivery"; RSC Advances; Royal Society of Chemistry; www.rsc.org/advances; DOI: 10.1039/c6ra16549d; Aug. 16, 2016; 7 pgs.
Liu, et al.; "Optimized synthesis and crystalline stability of γ-cyclodextrin metal-organic frameworks for drug adsorption"; Elsevier; International Journal of Pharmaceutics; www.elsevier.com/locate/ijpharm; Apr. 21, 2016; 8 pgs.
Liu, et al.; "Supporting Information for Optimized synthesis and crystalline stability of γ-cyclodextrin metal-organic frameworks for drug adsorption"; International Journal of Pharmaceutics; Sep. 29, 2016; 8 pgs.

\* cited by examiner

METHOD OF PREPARING CYCLODEXTRIN COMPLEXES

CROSS REFERENCE TO RELATED APPLICATION

Pursuant to 35 U.S.C. § 119(e), this application claims priority to U.S. Provisional Application Ser. No. 62/274,962, filed Jan. 5, 2016, the contents of which is hereby incorporated by reference in its entirety.

TECHNICAL FIELD

This application is directed, in general, to cyclodextrin complexes, and more specifically, methods of preparing cyclodextrin complexes, as well as related systems and products.

BACKGROUND

Cyclodextrins (e.g., cyclic dextrins, cyclic oligosaccharides, abbreviated herein as CDs) are cyclic structures composed of D-glucopyranosyl residues linked in a ring by α-1,4 glycosidic bonds. Glucose molecules, bonded together in the ring, form a hollow, circular, truncated cone with a hydrophobic interior and a hydrophilic exterior. This structure gives CDs the ability to host guest molecules (complexant) within their cavity (e.g., pore). The ability to form inclusion compounds (complexes) with a wide variety of chemicals, facilitates CDs to act as a carrier to encapsulate, stabilize, and/or alter the chemical and physical properties (e.g., volatility and solubility) of the guest molecules, CDs have been widely used in the agricultural, food, pharmaceutical, and chemical industries. Often, αCD, βCD, and γCD include six, seven, and eight glucopyranose units in their ring, respectively.

SUMMARY

A method embodiment of the disclosure comprises preparing an agent-cyclodextrin complex. Preparing the agent-cyclodextrin complex includes contacting a first composition comprising an agent with a porous cyclodextrin-metal organic framework to form a second composition comprising an agent-cyclodextrin-metal organic framework complex, the cyclodextrin-metal organic framework including a plurality of cyclodextrin molecules and at least one metal cation. Preparing the agent-cyclodextrin complex also includes dissolving the agent-cyclodextrin-metal organic framework complex in an aqueous solvent to form a third composition including the agent-cyclodextrin complex.

In some embodiments the cyclodextrin molecules of the porous cyclodextrin-metal organic framework includes one or more α cyclodextrin molecule, β cyclodextrin molecule, γ cyclodextrin molecule, or a mixture thereof. In some embodiments the agent includes one or more drug, fragrance, colorant, flavorant or vitamin. In some embodiments the agent has a water solubility of at most about 10 mg/mL at 25° C. In some embodiments the agent has an average diameter of about 10 Angstroms or less, about 7 Angstroms or less or about 5 Angstroms or less. In some embodiments, agent has pKa that is at least about 10 units, at least about 5 units or at least about 2 units lower than a pKa of base counter ions present in the porous cyclodextrin-metal organic framework.

In any of such embodiments, the aqueous solvent includes water, a water-miscible solvent, or a mixture thereof. Any such embodiments can further include providing the first composition containing the agent. In some such embodiments, providing the first composition includes preparing a salt of the agent. In some such embodiments, providing the first composition includes dissolving the agent in a solvent. Any such embodiments can further include providing the porous cyclodextrin-metal organic framework. In some such embodiments providing the porous cyclodextrin-metal organic framework includes providing a solid form of the porous cyclodextrin-metal organic framework. In some such embodiments, providing the porous cyclodextrin-metal organic framework includes dissolving the porous cyclodextrin-metal organic framework in an aqueous solvent containing a metal cation or a base.

Any such embodiments can further include drying the second composition to form a solid agent-cyclodextrin-metal organic framework complex prior to the dissolving of the agent-cyclodextrin-metal organic framework complex. In some embodiments the dissolving of the agent-cyclodextrin-metal organic framework complex includes forming a salt between the agent and metal cations provided with the porous cyclodextrin-metal organic framework. Any such embodiments can further include including isolating the agent-cyclodextrin complex from other components of the third composition and/or isolating a metal salt form of the agent from other components of the third composition.

BRIEF DESCRIPTION

The embodiments of the disclosure are best understood from the following detailed description, when read with the accompanying FIGUREs. Reference is now made to the following descriptions taken in conjunction with the accompanying drawings, in which.

DETAILED DESCRIPTION

Embodiments of the present disclosure benefit from the unexpected discovery that a cyclodextrin-metal organic frameworks (CD-MOFs) can be used as an intermediate to prepare CD complexes (e.g., drug CD complexes) with significantly improved efficiencies (e.g., higher yields), thereby significantly reducing the amounts waste product and reduce manufacturing costs for producing such CD complexes.

In particular, the present disclosure benefits from our discovery that intermediate agent-CD-MOF complexes can be prepared in higher concentrations than concentrations of agents-CD complexes formed by directly mixing agents and CDs together. Additionally, we discovered that the intermediate agent-CD-MOF complex can then be decomposed in an aqueous solvent to form high yielding amounts of the desired agent-CD complex. It is surprising or counterintuitive that higher yields of agent CD complex can be prepared by introducing extra steps, forming an intermediate agent-CD-MOF complex and then decomposing this intermediate complex, into the preparation method.

Figure 1:
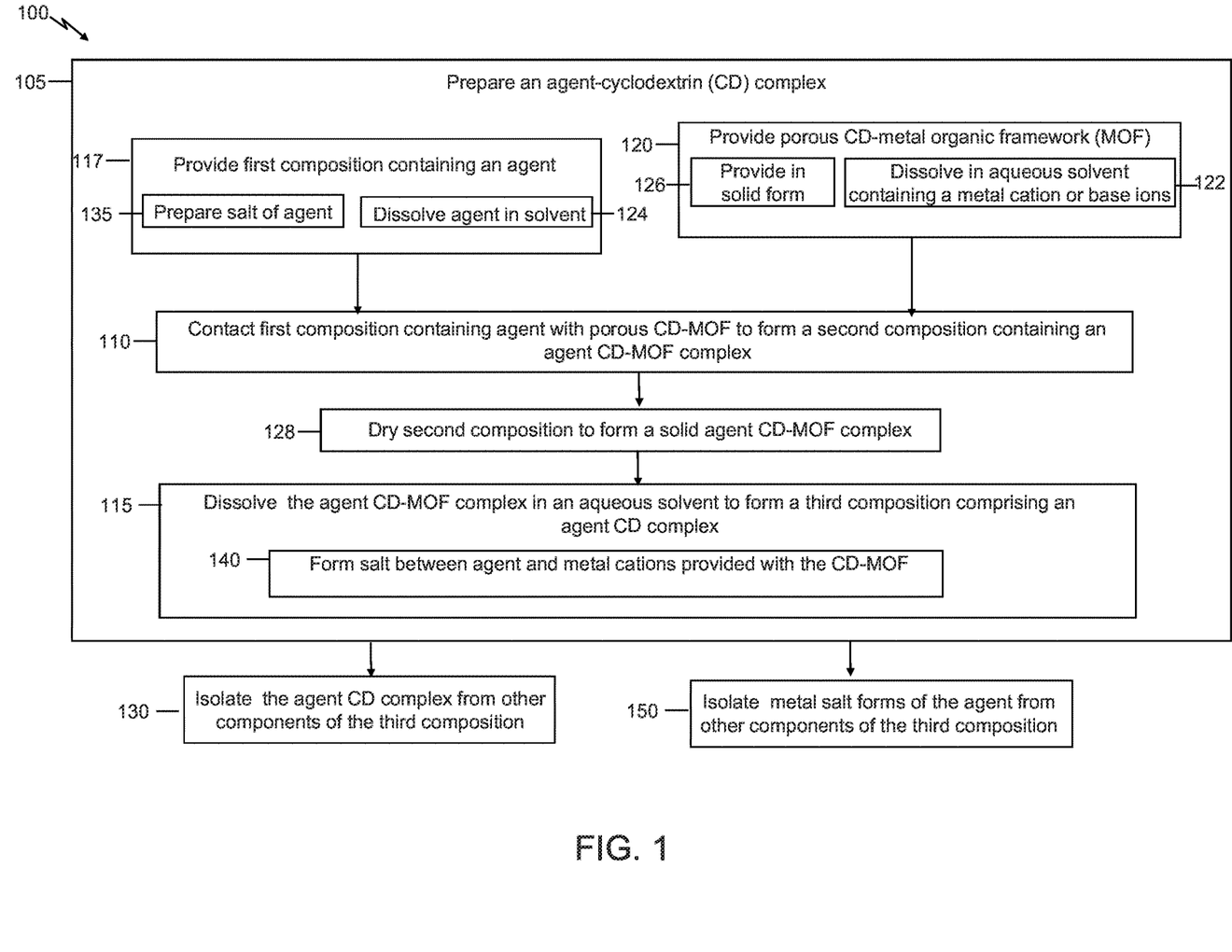
FIG. 1 presents a flow diagram of an example method of the disclosure comprising preparing a cyclodextrin complex.

FIG. 1 presents a flow diagram of an example method 100 of the disclosure comprising preparing an agent-cyclodextrin complex (step 105). As illustrated in FIG. 1, preparing the agent cyclodextrin complex in accordance with step 105 includes contacting a first composition containing an agent with a porous CD-MOF to form a second composition containing an agent CD-MOF complex (step 110). Preparing the cyclodextrin complex in accordance with step 105 also includes dissolving the agent CD-MOF complex in an aqueous solvent to form a third composition comprising an agent CD complex (step 115). That is, the agent CD complex of the third composition does not include the MOF component of CD-MOF.

The CD-MOF can include one or more of cyclodextrin molecules and at least one metal cation. As used herein, the term cyclodextrin includes α-, β- and γ-cyclodextrins, and their derivatives, e.g., such as those described in Formula (I) herein, or CD mixtures thereof.

Embodiments of the method 100 can further include providing a first composition containing an agent (step 117).

The term agent as used herein, and such as used in the preparation methods described herein can be any suitable substances, e.g., substances that benefit from improved water solubility, bioavailability, or other properties, such as having a size that can fit into a pore of the CD-MOF. For example, embodiments of the agent can have an average diameter (e.g., as determined by x-ray crystallography, size exclusion chromatography or other techniques familiar to those skilled in the pertinent arts) of about 5, 7 or 10 Angstroms of less so that the agent can fit into the pore of α-, β- and γ-CD-MOFs, respectively.

Examples of suitable embodiments of the agents include drugs, fragrances, colorants, flavors, vitamins, or combinations thereof. In some embodiments, the agent can consist of essentially of one of such agent embodiment, e.g., 99 wt % (or in some embodiments 99.9 or 99.99 wt %) of a single drug, fragrance, colorants, flavor or vitamin with only trace amounts of other molecules or atoms other than optional counter ions that form salts with the agent.

In some embodiments, the agent (e.g., drug), can have low water solubility at room temperature (25° C.). For example, embodiments of the drug can have a water solubility of at most about 10 mg/mL (e.g., at most about 5 mg/mL, at most about 1 mg/mL, at most about 0.5 mg/mL or at most about 0.1 mg/mL) and/or at least about 0.1 µg/mL (e.g., at least about 0.5 µg/mL, at least about 1 µg/mL, at least about 5 µg/mL, at least about 10 µg/mL, at least about 50 µg/mL, at least about 0.1 mg/mL, at least about 0.5 mg/mL, or at least about 1 mg/mL) at 25° C.

In some embodiments, the agent (e.g., drug) can be a weakly acidic. For example, the agent (e.g., drug) can have a pKa of at least about 1 (e.g., at least about 1.5, at least about 2, at least about 2.5, at least about 3, at least about 3.5, at least about 4, at least about 4.5, or at least about 5) and/or at most about 10 (e.g., at most about 9.5, at most about 9, at most about 8.5, at most about 8, at most about 7.5, at most about 7, at most about 6.5, at most about 6, at most about 5.5, or at most about 5).

In some embodiments, to facilitate forming salt forms of the agent (e.g., drug), the agent and bases of the CD-MOF can be selected such that the agent has a pKa that is at least about 2 units (and in some embodiment at least about 5 units or at least about 10 units, e.g., $\log_{10}$ units) lower that a pKa of base counter ions present in the CD-MOF. For instance, in some embodiments the CD-MOF can include alkali bases (e.g., KOH, NaOH) having a pKa of about 13 to 14. When the agent CD-MOF complex is dissolved in the aqueous solvent (e.g., step 115), the CD-MOF is thought to break apart into its individual components (e.g., base and cyclodextrins) and thereby free the base to form a salt form of the agent. For example a base of NaOH and drug embodiments of the agent corresponding to acetylsalicylic acid (e.g., pKa about 3.5) or salicylic acid (e.g., pKa about 3) can form the ionic salts of sodium acetylsalicylate and sodium salicylate, respectively.

Non-limiting examples of suitable drug embodiments of the agent that can be used in the preparation methods described herein include salicylic acid, acetylsalicylic acid, ibuprofen, naproxen, diazepam, hydrocortisone, phenytoin, adenosine, and hydrochlorothiazide.

Non-limiting examples of suitable fragrance embodiments of the agent that can be used in the preparation methods described herein include linalool, benzyl acetate, menthol, methyl anthranilate, limonene or combinations thereof.

Non-limiting examples of suitable colorant embodiments of the agent that can be used in the preparation methods described herein include anthocyanin, carotenoid, curcumin or combinations thereof.

Non-limiting examples of suitable flavorant embodiments of the agent that can be used in the preparation methods described herein include ethyl maltol, benzaldehyde, eugenol, ethyl vanillin, cinnamaldehyde, diacetyl or combinations thereof.

Non-limiting examples of suitable vitamin embodiments of the agent that can be used in the preparation methods described herein include tocopherol, ascorbic acid, retinol or combinations thereof.

Embodiments of the method 100 can further include providing a CD-MOF (step 120). The provided CD-MOFs that can be used in the preparation methods described herein can include the CD-MOFs described in U.S. Pat. No. 9,085,460 (herein referred to as the 460' patent), which is hereby incorporated by reference in its entirety.

The CD-MOFs used in the preparation methods described herein can include at least one metal cation (e.g., a plurality of metal cations) and a plurality of cyclodextrin components (such as those depicted in formula (I) herein). The at least one metal cation can be generally coordinated with the plurality of cyclodextrin molecules or cyclodextrin derivatives. The CD-MOFs have at least one pore.

Suitable metal cations that can be used in the CD-MOFs include Group I metal cations (e.g., $Na^+$, $K^+$, $Rb^+$, or $CS^+$), Group II metal cations (e.g., Me, $Ca^{2+}$, $Sr^{2+}$, or $Ba^{2+}$), and transition metal cations (e.g., $Mn^{4+}$, $Fe^{3+}$, $Co^{2+}$, $Ni^{2+}$, $Cu^{2+}$, or $Zn^{2+}$). The metal cations can be included into the CD-MOFs by using salts or bases as starting materials. Examples of suitable salts include KF, KCl, KBr, $K_2CO_3$, $K_2$(azobenzene-4,4'-dicarboxylate), $Na_2CO_3$, and $NaBPh_4$. Examples of suitable bases include KOH, NaOH, RbOH, and CsOH.

The CD-MOFs used in the preparation methods described herein include cyclodextrin, a cyclic oligosaccharide that includes monosaccharide residues linked in a circular ring. Suitable cyclodextrins that can be used in the CD-MOFs include, for example, α-, β- and γ-cyclodextrins and their derivatives. Example structures of α-1,4-linked D-glucopyranosyl residue that can be used to form a building block in a cyclodextrin and the structure of a γ-cyclodextrin ring are disclosed in the 460' patent. As understood by those skilled in the pertinent arts, cyclodextrins can be mass-produced through enzymatic degradation of a renewable source (e.g., starch).

The CD-MOFs used in the preparation methods described herein can be prepared (e.g., as part of step 120) by dissolution (step 122) of both the cyclodextrin component (e.g., γ-cyclodextrin) and the metal-containing component (e.g., a metal salt such as KCl) or a base containing a metal cation (e.g., KOH)) in an aqueous solvent (e.g., water) in which both have good solubility (e.g., 10 mg/mL or greater in water). For example some embodiments of α-, β- and γ-CD can have a solubility in water of about 145, 18, and 232 mg/mL, respectively. Isolation of the CD-MOF complex (e.g., as part of step 120) can be achieved by the addition of a poor solvent in which either of the above components has poor solubility (e.g., less than 10 mg/mL in water). Suitable example poor solvents include $C_1$-$C_{18}$ alcohols (e.g., methanol), acetone, tetrahydrofuran, dioxane, acetonitrile, or mixtures thereof.

In some embodiments, CD-MOFs used in the preparation methods described herein can be prepared as follows (e.g., provided as part of step 120). At ambient temperatures and pressures, γ-CD can be dissolved in an aqueous solution containing an alkali metal cation (e.g., $K^+$), and followed by vapor diffusion of a water-miscible solvent (e.g., methanol) to form millimeter-sized body-centered cubic crystalline structures.

Without limiting the scope of the disclosure by theoretical considerations, it is believed that the γ-CD rings can adopt the faces of a cube, with their primary (1°) faces (e.g., C6 hydroxy (OH) groups) pointing towards the interior of the cube and their secondary (2°) faces (e.g., C2 and C3 OH groups) pointing outward. Further, it is believed that the γ-CD rings are linked together by coordination of the alkali metal cations to the primary C6 OH groups and the glycosidic ring oxygen atoms. The individual cubes can pack to form the body-centered cubic crystal through coordination of more alkali metal cations to the C2 and C3 OH groups of the secondary faces of the γ-CD rings. Non-limiting examples of such CD-MOF geometries are disclosed in the 460' patent.

Embodiments of the CD-MOFs include a CD component and a metal-containing component. The metal-containing component can have the formula MN, where M can be a Group I, Group II metal or transition metal, and N can be an organic or inorganic, monovalent or multivalent anion. Non-limiting suitable inorganic anions include chloride, fluoride, hydroxide, sulfide, sulfinate, carbonate, chromate, and cyanide. Suitable organic anions include, for example, benzoate, azobenzene-4,4'-dicarboxylate, acetate, and oxalate. The CD component of the CD-MOFs can be a compound of the Formula (I):

Formula (I)

where n=0-10; R is selected from the group consisting of —OH; —NR'R"; $C_1$-$C_{18}$ alkyl optionally substituted with one, two, three, four or five $R_1$ groups; $C_2$-$C_{18}$ alkenyl optionally substituted with one, two, three, four or five $R_1$ groups; $C_2$-$C_{18}$ alkynyl optionally substituted with one, two, three, four or five $R_1$ groups; $C_1$-$C_{18}$ alkoxy optionally substituted with one, two, three, four or five $R_1$ groups; —S(=O)$_2$R'; —S(=O)OR'; S(=O)R'; —C(=O)OR'; —CN; —C(=O)R'; —SR', —N=N$^+$=N$^-$; —NO$_2$, —OSO$_2$R'; —C(=O)OR'; —O(=S)SR'; —P(=O)(OR')$_2$; —OP(=O)(OR')$_2$; —P(=O)(OR')R"; —N=R'R"; —NR'P(OR")(OR'"); —OC(=O)NR'R"; aryl optionally substituted with one, two, three, four or five $R_2$ groups; heteroaryl optionally substituted with one, two, three, four or five groups independently selected from $R_2$ groups; and cycloalkyl optionally substituted with one, two, three, four or five groups independently selected from $R_2$ groups; each $R_1$ group is independently selected from the group consisting of hydroxyl, halo, $C_1$-$C_6$ alkoxy, —NR'R"; —S(=O)$_2$R'; —S(=O)OR'; —S(=O)R'; C(=O)OR'; —CN; —C(=O)R'; —SR', —N=N$^+$=N$^-$; —NO$_2$, —OSO$_2$R'; —C(=O)OR'; —O(=S)SR'; —P(=O)(OR')$_2$; —OP(=O)(OR')$_2$; —P(=O)(OR')R"; —N=R'R"; —NR'P(OR")(OR'"); —OC(=O)NR'R"; aryl optionally substituted with one, two, three, four or five R' groups; heteroaryl optionally substituted with one, two, three, four or five groups independently selected from R' groups; and cycloalkyl optionally substituted with one, two, three, four or five groups independently selected from R' groups; each $R_2$ group is independently selected from the group consisting of $C_1$-$C_6$ alkyl, $C_2$-$C_6$ alkyenyl, $C_2$-$C_6$ alkynyl, hydroxyl, halo, $C_1$-$C_6$ alkoxy, —NR'R"; —S(=O)$_2$R'; —S(=O)OR'; —S(=O)R'; —C(=O)OR'; —CN; —C(=O)R'; —SR', —N=N$^+$=N$^-$; —NO$_2$, —OSO$_2$R'; —C(=O)OR'; —O(=S)SR'; —P(=O)(OR')$_2$; —OP(=O)(OR')$_2$; —P(=O)(OR')R"; —N=R'R";

—NR'P(OR")(OR'''); —OC(=O)NR'R"; aryl optionally substituted with one, two, three, four or five R' groups; heteroaryl optionally substituted with one, two, three, four or five groups independently selected from R' groups; and cycloalkyl optionally substituted with one, two, three, four or five groups independently selected from R' groups; and wherein each R', R", and R''' are independently selected from the group consisting of H, $C_1$-$C_6$ alkyl, and aryl. Examples of compounds of Formula (I) include α-, β- and γ-cyclodextrins.

As used herein, the term "alkyl" refers to a straight or branched chain alkyl radical. Examples include, but are not limited, to methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. Each alkyl group may be optionally substituted with one, two or three substituents such as a halo, cycloalkyl, aryl, alkenyl or alkoxy group.

As used herein, the term "lower alkenyl" refers to a straight or branched hydrocarbon radical having one or two double bonds and includes, for example, ethenyl, propenyl, 1-but-3-enyl, 1-pent-3-enyl, and 1-hex-5-enyl. The alkenyl group can also be optionally mono-, di-, or trisubstituted with, for example, halo, aryl, cycloalkyl or alkoxy.

As used herein, the term "alkynyl" refers to a straight or branched hydrocarbon radical having one or two triple bonds and includes, for example, propynyl and 1-but-3-ynyl. The alkynyl group can also be optionally mono-, di-, or trisubstituted with, for example, halo, aryl, cycloalkyl or alkoxy.

As used herein, the term "alkoxy" refers to an —O— alkyl group in which the alkyl is as defined above.

As used herein, the term "halo" or "halogen" refers to a halogen radical of fluorine, chlorine, bromine, or iodine.

As used herein, the term "aryl" refers to an aromatic carbocylic radical having a single ring (e.g. phenyl), multiple rings (e.g. biphenyl), or multiple fused rings in which at least one is aromatic (e.g. 1,2,3,4-tetrahydronaphthyl).

As used herein, the term "heteroaryl" refers to one aromatic ring or multiple fused aromatic ring systems of 5-, 6- or 7-membered rings containing at least one and up to four heteroatoms (e.g., nitrogen, oxygen or sulfur). Examples include, but are not limited to, furanyl, thienyl, pyridinyl, pyrimidinyl, benzimidazolyl and benzoxazolyl.

As used herein, the term "cycloalkyl" refers to a carbocylic radical having a single ring (e.g., cyclohexyl), multiple rings (e.g., bicyclohexyl) or multiple fused rings (e.g., decahydronaphthalenyl). In addition, the cycloalkyl group may have one or more double bonds.

In some embodiments, the first composition used in the preparation methods described herein can include a solvent in which the agent has been dissolved (e.g., step 124). The solvent can be an organic solvent, such as an alkane (e.g., hexane and mineral oils), an alcohol (e.g., $C_1$-$C_{18}$ alcohols such as methanol, ethanol, isopropanol, or propylene glycol), a ketone (e.g., acetone), an ester (e.g., ethyl acetate), an ether (e.g., ethyl ether, a glycol ether, tetrahydrofuran, or dioxane), a nitrile (e.g., acetonitrile), and a mixture thereof.

In some embodiments, the CD-MOF (e.g., provided as part of step 120) used in the preparation methods described herein can be provided in a solid form (step 126), such as a crystal or a powder. In such embodiments, while not limiting the scope of the disclosure by theoretical considerations it is believed that contacting the first composition containing the agent with the CD-MOF (e.g., step 110) can load the agent molecules into the pores of the CD-MOF, thereby forming the second composition containing the agent CD-MOF complex. In some such embodiments, the agent in the agent CD-MOF complex may form coordinate bonds with the CD-MOF (e.g., a covalent bond of a shared pair of electrons in which both electrons come from the same atom of the CD-MOF). In some such embodiments, the agent of the agent CD-MOF complex may be secured in the pores in the CD-MOF by other intermolecular interactions (e.g., hydrogen bonding, hydrophobic interaction, or van der Waals force) without forming any coordinate bond with the CD-MOF.

In some embodiments, the second composition formed as described herein (e.g. step 110) can be dried (step 128) by any suitable method (e.g., by air, vacuum, or heating) to form a solid agent CD-MOF complex and remove other components of the second composition (e.g., solvents used to dissolve the agent in step 122 and/or dissolve the CD-MOF as part of step 120.

As noted above forming the third composition containing an agent CD complex (e.g., as part of step 115) includes dissolving the agent CD-MOF complex in an aqueous solvent. In some embodiments, the aqueous solvent can include water, a water-miscible solvent (e.g., ethanol, or a water ethanol mixture).

While not limiting the scope of the disclosure by theoretical considerations, it is believed that when the agent CD-MOF complex is dissolved in the aqueous solvent (e.g., water), the CD-MOF decomposes and generates free cyclodextrin, and metal cations and corresponding anions. Further it is believed that by using a CD-MOF as an intermediate in the formation of the third composition facilitates the agent molecules being located in close proximity to the free cyclodextrin and/or metal cations when the agent CD-MOF decomposes in the aqueous solvent, e.g., by virtue of being located in the pore of the CD-MOF. For example, an agent molecule in a pore of a CD-MOF can be within about 10 Angstrom of the cyclodextrin ring and/or metal cations of the CD-MOF. It is further believed that such close proximity of the agent and the free cyclodextrin and/or metal cations can facilitate the formation of an agent CD complex and/or a salt form of the agent, thereby significantly improving the efficiencies (e.g., yields) in preparing agent CD complexes (e.g., drug CD complexes) and/or salt forms of the agent.

While not limiting the scope of the disclosure by theoretical considerations, it is believed that for some embodiments of the method, the agent CD complex can be more effectively made in higher yields as compared to mixing the agent and the corresponding CD in the aqueous solvent directly without using a CD-MOF as an intermediate. For example, it is believed that the amount of the agent CD complex in the third composition can be made in significantly higher amounts than the amount of an agent CD complex in a composition prepared by mixing the agent and the corresponding CD in an aqueous solvent directly as compared to when the same amounts of ingredients (e.g., the same amounts of the agent and CD) are used in the form of CD-MOF.

In some embodiments, the preparation method 100 can further include isolating the agent CD complex from other components in the third composition (e.g., step 130). In some embodiments, for example, the agent CD complex can be isolated by using column chromatography, filtration, and/or centrifugation.

In some embodiments, the method can further include preparing a salt form of the agent (e.g., drug) (step 135). For example, in step 110, the method 100 can include contacting a first composition containing a drug with a porous cyclodextrin-metal organic framework (CD-MOF) to form a second composition containing a drug CD-MOF complex. The CD-MOF can include a plurality of cyclodextrin molecules and at least one metal cation. The drug can be acidic and have a pKa of at least about 1. In such embodiments, the drug and CD-MOF can have the properties and/or characteristics described above. For example, the first composition can contact the CD-MOF in a solid form (e.g., a crystal or a powder, such as provided in step 120) to form the second composition.

In some embodiments, the first composition containing the agent (e.g., a drug) can further include a solvent (such as the organic solvent described above in the context of step 124), e.g., in which the drug can be dissolved before loading onto a CD-MOF to form a drug CD-MOF complex.

In some embodiments, the method 100 as part of step 128, can further include drying the second composition (e.g., by removing the solvent from the second composition) to form a solid agent (e.g., drug) CD-MOF complex. The drying can be performed by any suitable means.

In some embodiments, the method 100 as part of step 115 can further include dissolving the solid agent CD-MOF complex (e.g., after drying step 128) in an aqueous solvent to form (e.g., step 140) the third composition containing a salt form of the agent (e.g., a salt form of a drug), in which the salt is formed between the agent and metal cation provided with the porous CD-MOF (e.g., as part of step 120).

In some embodiments, the method 100 can further include isolating the salt form of the drug from other components (e.g., CD and MOF components) of the third composition (step 150). In some embodiments, the salt can be isolated by using crystallization, solvent extraction, and/or column chromatography.

The methods of preparing an agent (e.g., drug) salt form described above can be used to prepare salt forms of certain agent (e.g., those having a relatively low water solubility) and whose salts are otherwise difficult to prepare in high yields. For example, salt forms of certain drugs may have a greater tendency to absorb water than associate with the corresponding free acid or base to form a salt. In such cases, the salt form of these drugs tends to be more unstable and more hygroscopic than the drugs themselves such that they cannot be handled easily and can have a short shelf life. As another example, certain compounds such as potassium hydroxide are so hygroscopic that they can dissolve in humid air.

For example, forming a salt form of certain agents (e.g., drugs such as aspirin) with potassium hydroxide can be difficult. However, using a CD-MOF as an intermediate can facilitate forming a stable drug CD-MOF complex, which can be stored for relatively long time periods (e.g., weeks or months). For example a drug CD-MOF complex can be used to facilitate making a salt form of the drug (e.g., by adding the drug CD-MOF complex in an aqueous solvent) immediately before the salt form of the drug is used (e.g., administered to a patient). For example, upon dissolution of the drug CD-MOF complex (e.g., an aspirin-loaded CD-MOF) in water, the complex can be decomposed to form the drug, the CD, and the metal cation used to form the CD-MOF such that the drug can react with the metal cation (e.g., the potassium cation in potassium hydroxide) to form a salt of the drug due the close proximity of the drug and the metal cation in the drug CD-MOF complex (e.g., in the pore of the CD-MOF). It is believed that this approach can help overcome hygroscopic issues associated with certain compounds (e.g., potassium hydroxide) by storing such compounds in a drug CD-MOF complex.

In some embodiments, the preparation methods described herein can be used to improve the loading efficiency of the agent into a CD. When the agent is a drug, the preparation methods described herein can also be used to improve the bioavailability of the drug. In some embodiments, the preparation methods described herein can be used to prepare an agent CD complex or a salt form of an agent immediately before the agent is used. In such embodiments, the shelf life of the agent can be significantly improved.

Some non-limiting aspects of the disclosure are illustrated in the examples to follow to demonstrate how amounts of the agent CD complex in the third composition can be higher than amounts of an agent CD complex in a composition prepared by mixing the agent and the CD in an aqueous solvent, without using the porous CD-MOF as an intermediate, when the same amounts of ingredients are used.

Example Preparation of CD-MOFs

CD-MOF crystals were prepared following a similar procedure as described in U.S. Pat. No. 9,085,460. Specifically, CD-MOF crystals were grown through vapor diffusion of methanol into an aqueous solution of gamma-cyclodextrin and potassium hydroxide. The crystals were left to grow for a period of about 1 to 2 weeks, after which they were collected, filtered, washed with methanol, and then evacuated in a vacuum chamber at room temperature to approximately $10^{-3}$ Torr for 24 hours. The CD-MOF crystals were then used in the following experiments without further purification.

Example Preparations of Agent CD-MOF Complexes

To measure the increase in water solubility of a drug by employing a CD-MOF, salicylic acid (a weak acidic drug) was used as an example and was loaded into the CD-MOF prepared above at specific loading weight percentages. Specifically, salicylic acid was first dissolved in ethanol at 1 gram per 10 mL ethanol. The amount of salicylic acid solution used in different samples below was based on the targeted loading percentage by weight. For example, to achieve 10% loading by weight, 10 mg of salicylic acid was loaded into a 100 mg CD-MOF sample. After loading the CD-MOF sample with the salicylic acid ethanol solution, the sample was dried to evaporate the ethanol, leaving a dry γCD-MOF powder loaded with salicylic acid.

The dry, loaded CD-MOF samples were then dissolved in 10 mL water and stirred. UV-VIS spectroscopy was measured for aliquots taken from the solution to determine the amount of salicylic acid dissolved in the aqueous solution.

We believe that when salicylic acid is loaded into the CD-MOF samples, the drug molecules diffuse and are positioned within the internal pore spaces of the CD-MOF crystals. When the loaded CD-MOF crystals are dissolved in water, the CD-MOF breaks apart and generates free cyclodextrin, potassium ions, and hydroxide ions. It is believed that, by using a CD-MOF as an intermediate, salicylic acid molecules can be located at close proximity to the cyclodextrin and potassium hydroxide molecules in water.

As a result, we believe that salicylic acid formed by this approach can be more soluble in water, as compared to a conventional method without using a CD-MOF, for at least two reasons: 1) salicylic acid molecules can form inclusion complexes with the cyclodextrin molecules more easily due to their close proximity, and 2) salicylic acid can react with potassium hydroxide to form a more soluble salt form (i.e., potassium salicylate) more easily due to their close proximity. For low loading percentage, it is believed that the amount of salicylic acid that is solubilized in water can be relatively high because there are more than enough cyclodextrin and potassium hydroxide molecules to form complexes or react with salicylic acid. However, it is believed that, as the loading percentage increases, the amount of salicylic acid molecules can eventually exceed the amount of available cyclodextrin and/or potassium hydroxide, thereby leaving un-complexed and un-reacted salicylic acid. It is believed that, as this un-complexed and un-reacted salicylic acid is less soluble in water, the total amount of solubilized salicylic acid would reach a maximum value.

All water solubility shown in FIGS. 2-4 below were measured at room temperature. As references, the water solubility of salicylic acid was compared in samples prepared by adding suitable amounts of salicylic acid in water without any additive and in samples prepared by adding suitable amounts of salicylic acid in an aqueous solution containing γCD and KOH.

Figure 2:
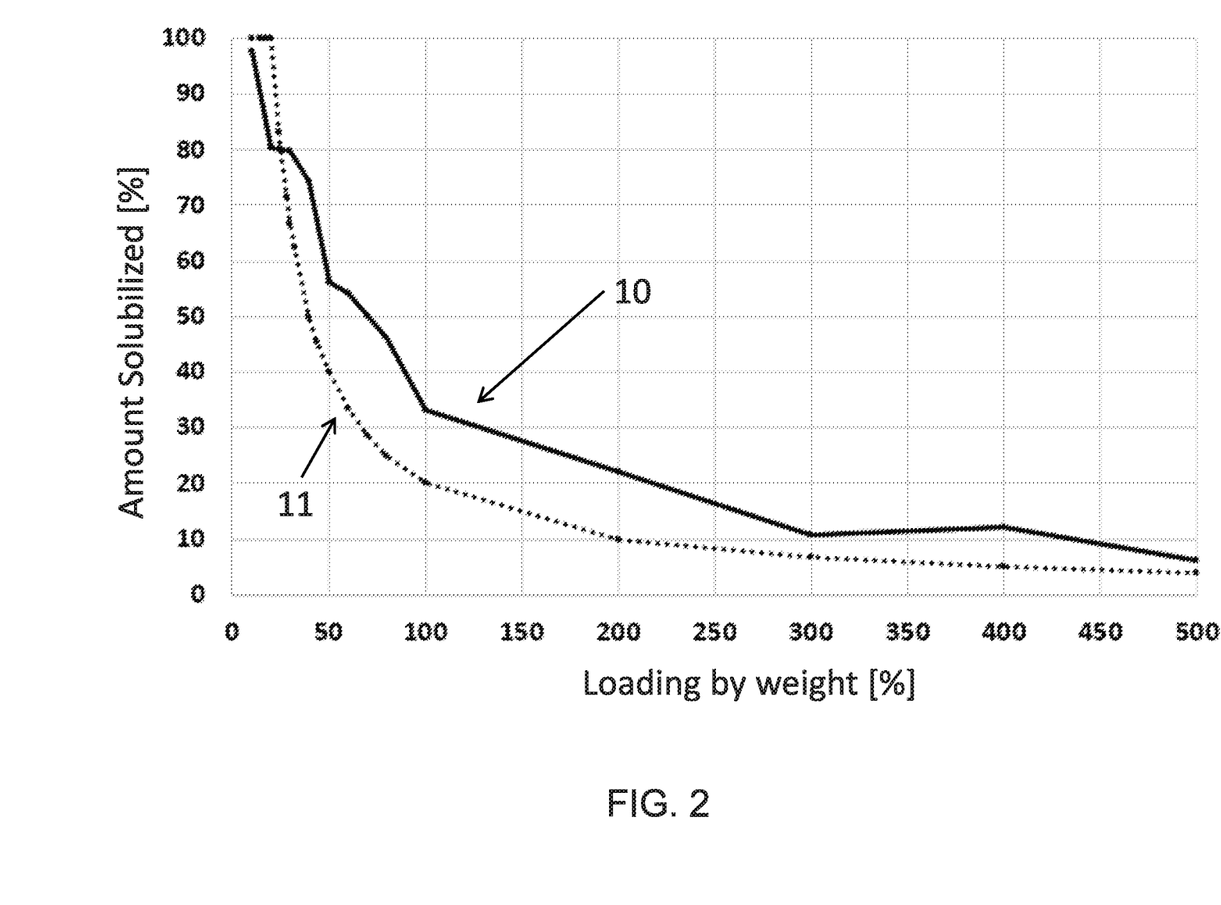
FIG. 2 presents a graph containing curves showing: (1) the percentage of solubilized salicylic acid in 10 mL of water versus the loading percentage of salicylic acid in 100 mg of a γCD-MOF (curve 10), and (2) the percentage of solubilized salicylic acid versus the percentage of salicylic acid added in 10 mL of water calculated based on 100 mg of salicylic acid in the absence of any additive (such as a CD-MOF) (curve 11)

FIG. 2 presents a graph containing curves showing (1) the percentage of solubilized salicylic acid in 10 mL of water versus the loading percentage of salicylic acid in 100 mg of a γCD-MOF (curve 10), and (2) the percentage of solubilized salicylic acid versus the percentage of salicylic acid added in 10 mL of water, calculated based on 100 mg of salicylic acid in the absence of any additive (such as a CD-MOF) (curve 11). As an example, in the x-axis, 500% in curve 10 represents 500 mg of salicylic acid loaded in a 100 mg CD-MOF sample. For curve 11, 500% in the x-axis represents 500 mg of salicylic acid added into 10 mL water without any CD-MOF.

As shown in curves 10 and 11 in FIG. 2, when a 100 mg CD-MOF sample was used, the percentage of solubilized salicylic acid in 10 mL of water was higher over the loading percentage range of about 25-500% (especially in the range of about 25-300%) than the percentage of solubilized salicylic acid in 10 mL of water in the absence of any additive (such as a CD-MOF).

Figure 3:
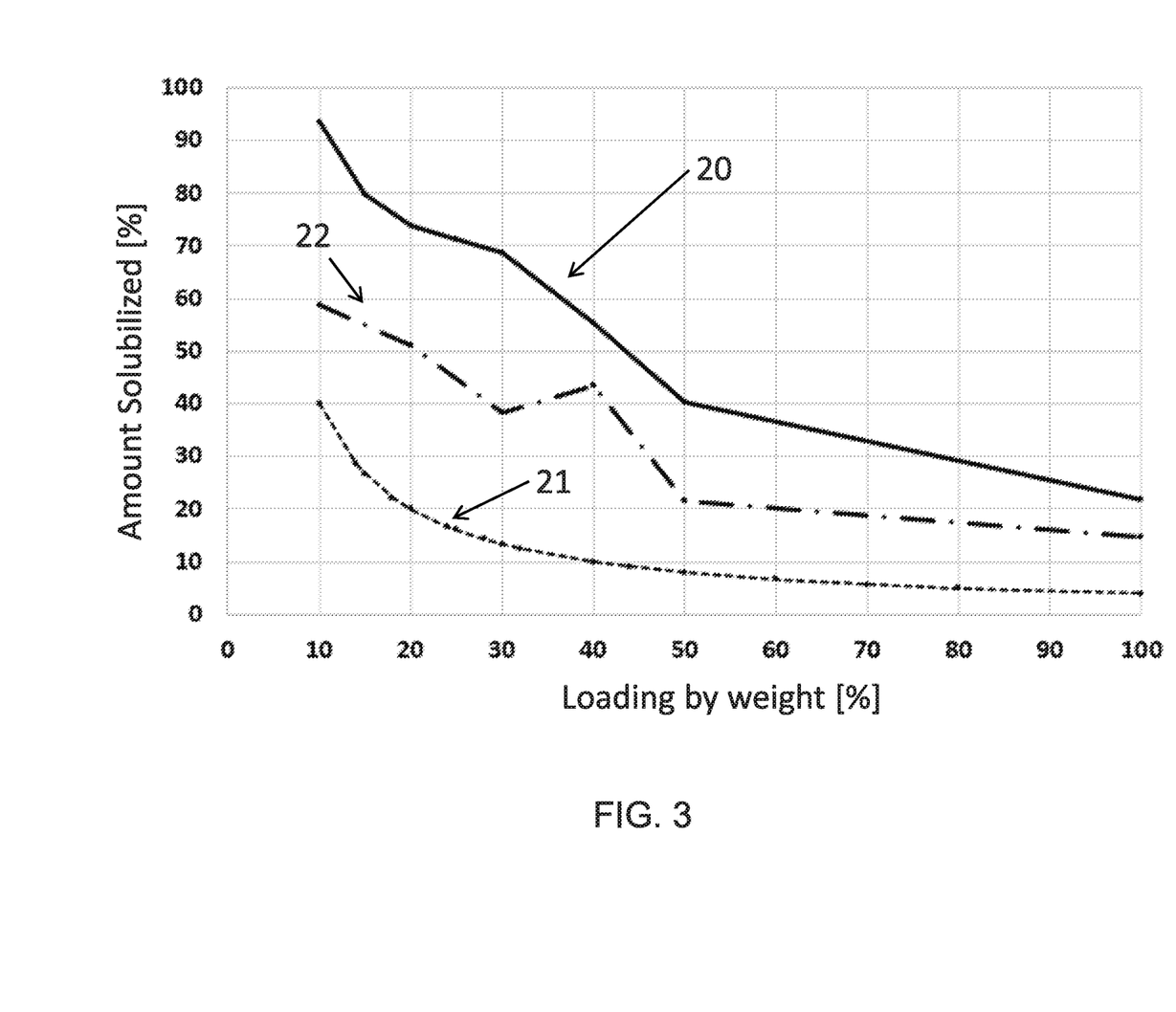
FIG. 3 presents a graph containing curves showing: (1) the percentage of solubilized salicylic acid in 10 mL of water versus the loading percentage of salicylic acid in 500 mg of a γCD-MOF (curve 20), (2) the percentage of solubilized salicylic acid versus the percentage of salicylic acid added in 10 mL of water calculated based on 500 mg of salicylic acid in the absence of any additive (such as a CD-MOF) (curve 21), and (3) the percentage of solubilized salicylic acid in 10 mL of water versus the loading percentage of salicylic acid in a 500 mg sample containing equivalent amounts of γCD and KOH (curve 22)

FIG. 3 presents a graph containing curves showing (1) the percentage of solubilized salicylic acid in 10 mL of water versus the loading percentage of salicylic acid in 500 mg of a γCD-MOF (curve 20), (2) the percentage of solubilized salicylic acid versus the percentage of salicylic acid added in 10 mL of water calculated based on 500 mg of salicylic acid in the absence of any additive (such as a CD-MOF) (curve 21), and (3) the percentage of solubilized salicylic acid in 10 mL of water versus the loading percentage of salicylic acid in a 500 mg sample containing equivalent amounts of γCD and KOH (curve 22). The amounts of γCD and KOH used to obtain curve 22 are identical to the amounts of γCD and KOH used to prepare the γCD-MOF in curve 20. As an example, in the x-axis, 100% in curve 20 or curve 22 represents 500 mg of salicylic acid loaded in a 500 mg CD-MOF sample or a 500 mg sample containing γCD and KOH. For curve 21, 100% in the x-axis represents 100 mg salicylic acid added in water without any CD-MOF.

As shown in FIG. 3, the percentage of solubilized salicylic acid in 10 mL of water when a 500 mg CD-MOF sample was used (curve 20) was significantly higher over the entire tested loading percentage of 10-100% than the percentage of solubilized salicylic acid in 10 mL of water in the absence of any additive (curve 21) and the percentage of solubilized salicylic acid in 10 mL of water in the presence of a 500 mg sample containing equivalent amounts of γCD and KOH (curve 22). For example, as shown in FIG. 3, when 30% salicylic acid is loaded into a 500 mg CD-MOF sample, of the 150 mg of salicylic acid loaded into the CD-MOF powder, about 69% (or about 103 mg) of salicylic acid was solubilized in 10 mL of water. This solubility is much higher than: (1) the solubility of un-complexed salicylic acid in water in the absence of a CD-MOF, which was approximately 13% (or about 20 mg) in 10 mL of water at room temperature and (2) the solubility of salicylic acid added directly into a solution containing equivalent amounts of γCD and KOH, which was approximately 39% (or about 58.5 mg) in 10 mL of water at room temperature. That is, FIG. 3 shows that using a CD-MOF as an intermediate can form a salicylic acid CD complex with a much higher efficiency than forming a salicylic acid CD complex by adding salicylic acid directly into a solution containing equivalent amounts of CD and KOH, and can significantly improve the solubility of salicylic acid in water compared to adding salicylic acid in water without any additive or adding salicylic acid in an aqueous solution containing γ equivalent amounts of a CD and KOH.

Figure 4:
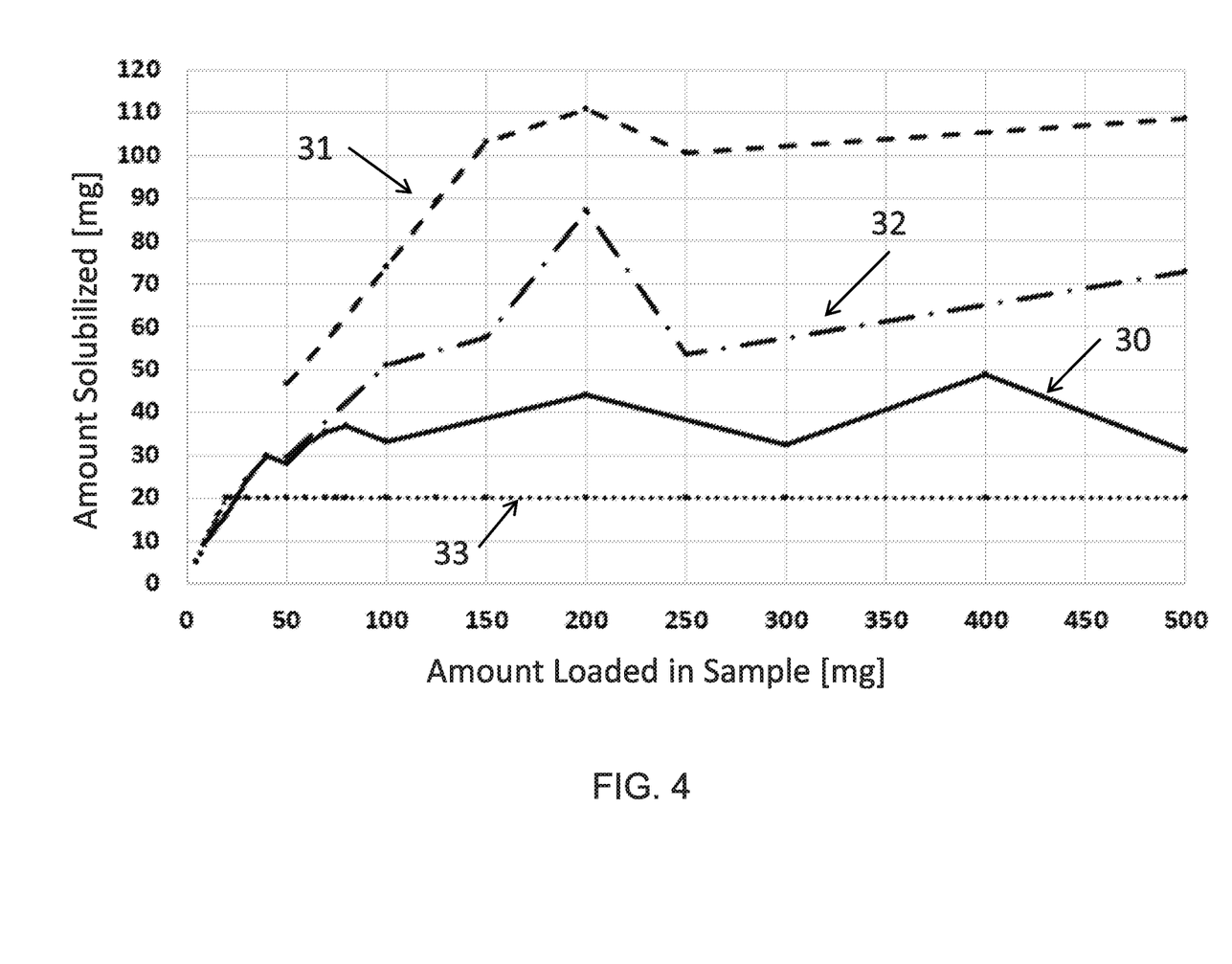
FIG. 4 presents a graph containing curves showing: (1) the amount of solubilized salicylic acid in 10 mL of water versus the loading amount of salicylic acid in 100 mg of a γCD-MOF (curve 30), (2) the amount of solubilized salicylic acid in 10 mL of water versus the loading amount of salicylic acid in 500 mg of a γCD-MOF (curve 31), (3) the amount of solubilized salicylic acid in 10 mL of water versus the loading amount of salicylic acid in a 500 mg sample containing equivalent amounts of γCD and KOH (curve 32), and (4) the amount of solubilized salicylic acid in 10 mL of water versus the amount of salicylic acid added in 10 mL of water in the absence of any additive (such as a CD-MOF) (curve 33).

FIG. 4 presents a graph containing curves showing: (1) the amount of solubilized salicylic acid in 10 mL of water versus the loading amount of salicylic acid in 100 mg of a γCD-MOF (curve 30), (2) the amount of solubilized salicylic acid in 10 mL of water versus the loading amount of salicylic acid in 500 mg of a γCD-MOF (curve 31), (3) the amount of solubilized salicylic acid in 10 mL of water versus the loading amount of salicylic acid in a 500 mg sample containing equivalent amounts of γCD and KOH (curve 32), and (4) the amount of solubilized salicylic acid in 10 mL of water versus the amount of salicylic acid added in 10 mL of water in the absence of any additive (such as a CD-MOF) (curve 33).

As shown in curve 33 in FIG. 4, the amount of salicylic acid dissolved in 10 mL of water in the absence of any additive reaches a maximum value at about 20 mg. By contrast, curves 30 and 31 show that, using a CD-MOF as an intermediate can significantly increase the solubility of salicylic acid in water (e.g., up to about 110 mg when a 500 mg CD-MOF sample was used). In addition, curve 31 and curve 32 show that using a CD-MOF as an intermediate can significantly increase the solubility of salicylic acid in water compared to adding salicylic acid directly into an aqueous solution containing equivalent amounts of a CD and KOH, suggesting that the former approach can form a salicylic acid CD complex with a much higher efficiency.

Those skilled in the art to which this application relates will appreciate that other and further additions, deletions, substitutions and modifications may be made to the described embodiments.

What is claimed is:
1. A method, comprising:
preparing an agent-cyclodextrin complex, including:
contacting a first composition comprising an agent with a porous cyclodextrin-metal organic framework to form a second composition comprising an agent-cyclodextrin-metal organic framework complex, the cyclodextrin-metal organic framework including a plurality of cyclodextrin molecules and at least one metal cation wherein:
the porous cyclodextrin-metal organic framework includes one of α cyclodextrin, β cyclodextrin, or γ cyclodextrin,
the agent includes one or more drug agent of: salicylic acid, acetylsalicylic acid, ibuprofen, naproxen, diazepam, hydrocortisone, phenytoin, adenosine, or hydrochlorothiazide, one or more fragrance agent of: linalool, benzyl acetate, menthol, methyl anthranilate, or limonene, one or more colorant agent of: anthocyanin, carotenoid, or curcumin, one or more flavorant agent of: ethyl maltol, benzaldehyde, euge- nol, ethyl vanillin, cinnamaldehyde, or diacetyl, or one or more vitamin agent of: tocopherol, ascorbic acid, or retinol, and the metal cation is $Na^+$, $K^+$, $Rb^+$, $CS^+$, $Mg^{2+}$, $Ca^{2+}$, $Sr^{2+}$, $Ba^{2+}$, $Mn^{4+}$, $Fe^{3+}$, $Co^{2+}$, $Ni^{2+}$, $Cu^{2+}$, or $Zn^{2+}$; and dissolving the agent-cyclodextrin-metal organic framework complex in an aqueous solvent to decompose the agent-cyclodextrin-metal organic framework complex and to form a third composition including the agent-cyclodextrin complex wherein:

the cyclodextrin is the one of α cyclodextrin, β cyclodextrin, or γ cyclodextrin, and for a loading percentage of the agent in a range of 10 to 100 weight percent of the agent relative to the cyclodextrin-metal organic framework in the second composition, an amount of the agent-cyclodextrin complex solubilized in the aqueous solvent is at least 5 percent greater in the third composition as compared to an amount of the agent-cyclodextrin complex in a sample solubilized in a same aqueous solvent containing equivalent amounts of same ones of the cyclodextrin molecule and the metal cation as present in the second composition.

2. The method of claim 1, wherein the agent has a water solubility of at most about 10 mg/mL at 25° C.

3. The method of claim 1, wherein the cyclodextrin molecule is γ cyclodextrin and the agent has an average diameter of about 10 Angstroms or less.

4. The method of claim 1, wherein the cyclodextrin molecule is β cyclodextrin and the agent has an average diameter of about 7 Angstroms or less.

5. The method of claim 1, wherein the cyclodextrin molecule is α cyclodextrin and the agent has an average diameter of about 5 Angstroms or less.

6. The method of claim 1, wherein the agent has a pKa that is at least about 10 units lower than a pKa of base counter ions present in the porous cyclodextrin-metal organic framework.

7. The method of claim 1, wherein the agent has a pKa that is at least about 2 units lower than a pKa of base counter ions present in the porous cyclodextrin-metal organic framework.

8. The method of claim 1, wherein the aqueous solvent includes water, a water-miscible solvent, or a mixture thereof.

9. The method of claim 1, further including providing the first composition containing the agent.

10. The method of claim 9, wherein providing the first composition includes preparing a salt of the agent.

11. The method of claim 9, wherein providing the first composition includes dissolving the agent in a solvent.

12. The method of claim 1, further including providing the porous cyclodextrin-metal organic framework.

13. The method of claim 12, wherein providing the porous cyclodextrin-metal organic framework includes providing a solid form of the porous cyclodextrin-metal organic framework.

14. The method of claim 12, wherein providing the porous cyclodextrin-metal organic framework includes dissolving the porous cyclodextrin-metal organic framework in an aqueous solvent containing a metal cation or a base.

15. The method of claim 1, further including drying the second composition to form a solid agent-cyclodextrin-metal organic framework complex prior to the dissolving of the agent-cyclodextrin-metal organic framework complex.

16. The method of claim 1, wherein the dissolving of the agent-cyclodextrin-metal organic framework complex includes forming a salt between the agent and metal cations provided with the porous cyclodextrin-metal organic framework.

17. The method of claim 1, further including isolating the agent-cyclodextrin complex from other components of the third composition.

18. The method of claim 1, further including isolating a metal salt form of the agent from other components of the third composition.

19. The method of claim 1, wherein for the loading percentage of the agent in a range 40 to 80 weight percent, the amount of the agent-cyclodextrin complex solubilized in the aqueous solvent is at least 10 percent greater in the third composition as compared to the amount of the agent-cyclodextrin complex in the reference sample.

20. A method, comprising:

preparing an agent-cyclodextrin complex, including:

contacting a first composition comprising an agent with a porous cyclodextrin-metal organic framework to form a second composition comprising an agent-cyclodextrin-metal organic framework complex, the cyclodextrin-metal organic framework including a plurality of cyclodextrin molecules and a metal cation, wherein the cyclodextrin is γ-cyclodextrin, the metal cation is $K^+$ or $Na^+$, and the agent is salicylic acid or acetylsalicylic acid; and dissolving the agent-cyclodextrin-metal organic framework complex in an aqueous solvent to decompose the agent-cyclodextrin-metal organic framework complex and to form a third composition including the agent-cyclodextrin complex, wherein for a loading percentage of the agent in a range 10 to 100 weight percent of the agent relative to the cyclodextrin-metal organic framework in the second composition, an amount of the agent-cyclodextrin complex solubilized in the aqueous solvent is at least 5 percent greater in the third composition as compared to an amount of the agent-cyclodextrin complex in a sample solubilized in a same aqueous solvent containing equivalent amounts of same ones of the cyclodextrin molecule and the metal cation as present in the second composition.

* * * * *